United States Patent
Bertrand et al.

(10) Patent No.: US 7,456,320 B2
(45) Date of Patent: Nov. 25, 2008

(54) PROCESS FOR THE SYNTHESIS OF SUBSTITUTED ALPHA-AMINOINDAN DERIVATIVES

(75) Inventors: Blandine Bertrand, Angrie (FR); Sylvie Blanchet, Feneu (FR); Alain Burgos, Les Ponts-de-Ce (FR); Juliette Martin, Aramon (FR); Florence Perrin, Avrille (FR); Sonia Roussiasse, Champigné (FR); Yvon Derrien, La Meignanne (FR)

(73) Assignee: ZaCh System, Avrille (FR)

( * ) Notice: Subject to any disclaimer, the term of this patent is extended or adjusted under 35 U.S.C. 154(b) by 0 days.

(21) Appl. No.: 10/589,529

(22) PCT Filed: Feb. 21, 2005

(86) PCT No.: PCT/IB2005/000534

§ 371 (c)(1), (2), (4) Date: Aug. 15, 2006

(87) PCT Pub. No.: WO2005/082838

PCT Pub. Date: Sep. 9, 2005

(65) Prior Publication Data

US 2007/0191640 A1    Aug. 16, 2007

(30) Foreign Application Priority Data

Feb. 19, 2004    (EP)    ................... 04290444

(51) Int. Cl.
*C07C 209/62*    (2006.01)

(52) U.S. Cl. .................................................. 564/414
(58) Field of Classification Search .................. None
See application file for complete search history.

(56) References Cited

U.S. PATENT DOCUMENTS 7,262,326 B2 *    8/2007    Blanchet et al. ............. 564/219

FOREIGN PATENT DOCUMENTS

| WO | 98/27055 | | 6/1998 |
| WO | 99/18065 | * | 4/1999 |

OTHER PUBLICATIONS

Zhang et al., J. Org. Chem. (1999), 64, p. 1774-1775.*
Tang et al., Org. Letters (2002), 4(10), p. 1695-1698.*
Evans et al., J. Am. Chem. Soc. (2003), 125(12), p. 3534-3543.*
Yonehara et al., J. Org. Chem. (1999), 64, p. 9381-9385.*
Zhu et al., J. Org. Chem. (1998), 63, p. 9590-9593.*
Burk et al., J. Org. Chem. (1998), 63, p. 6084-6085.*

* cited by examiner

*Primary Examiner*—Brian J Davis
(74) *Attorney, Agent, or Firm*—Merchant & Gould P.C.

(57) ABSTRACT

A process for the preparation of optically active substituted alpha-amino-indane derivatives of formula (I), which include: an asymmetric hydrogenation reaction of an enamide derivative of formula (III) in presence of hydrogen and an optically active catalyst, in order to obtain an amide derivative of formula (II), a hydrolysis reaction of the amide derivative of formula (II) obtained in the previous step, in order to obtain optically active substituted alpha-amino-indane derivatives of formula (I).

33 Claims, 1 Drawing Sheet

PROCESS FOR THE SYNTHESIS OF SUBSTITUTED ALPHA-AMINOINDAN DERIVATIVES

BACKGROUND OF THE INVENTION

This invention relates to a new process to prepare optically active substituted alpha-amino-indan derivatives useful as synthetic intermediates for the preparation of active pharmaceuticals.

According to the prior art document WO98/27055, optically active substituted alpha-amino-indane derivatives are prepared from an optically active non-substituted alpha-amino-indane with a four step process in order to obtain optically active alpha-amino-indan substituted compounds. This process involves a Friedel & Craft reaction and a Bayer-Villiger reaction. However, these two reactions show some limitations such as low yields and safety issues.

According to this document optically active substituted alpha-amino-indan derivatives are also prepared from a racemic substituted alpha-amino-indan compounds with an optical resolution process. The limitations of this process are the low yields.

SUMMARY OF THE INVENTION

This invention describes a new process for yielding to optically active substituted alpha-amino-indane compounds of general formula (I):

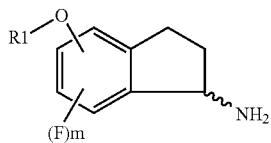

(I)

wherein:

m is an integer equal to 0, 1, 2 or 3, preferably m is 0, $R_1$ is a hydrogen atom, an alkyl group having from 1 to 20 carbon atoms, an aryl group having from 6 to 20 carbon atoms, an alkylaryl group having from 6 to 20 carbon atoms, an alkaloyl group, an aryloyl group, preferably R1 is an alkyl group having from 1 to 20 carbon atoms, and more preferably R1 is an alkyl group having from 1 to 4 carbon atoms, especially a methyl group, which comprise:

an asymmetric hydrogenation reaction of an en-amide derivative of formula (III)

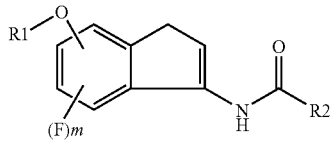

(III)

wherein m and R1 are as defined above,

R2 is a hydrogen atom, an alkyl group having from 1 to 20 carbon atoms, an aryl group having from 6 to 20 carbon atoms, an alkylaryl group having from 6 to 20 carbon atoms, preferably R2 is an alkyl group having from 1 to 20 carbon atoms, and more preferably an alkyl group having from 1 to 4 carbon atoms, especially a methyl in presence of hydrogen and an optically active catalyst, preferably an optically active asymmetric hydrogenation catalyst, in order to obtain an amide derivative of formula (II):

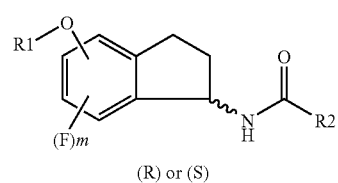

(II)

(R) or (S)

a hydrolysis reaction of the amide derivative of formula (II) obtained in the previous step, in order to obtain optically active substituted alpha alpha-amino indane derivatives of formula (I).

The derivatives of formula (I) can be in a (R) configuration or in a (S) configuration. In the same way, the derivatives of formula (II) can be in a (R) configuration or in a (S) configuration.

In the present application the term alkyl means a straight or branched alkyl group having from 1 to 20 carbon atoms (such as but not limited to methyl, ethyl, n-propyl, isopropyl, n-butyl, iso-butyl, sec-butyl, tert-butyl), optionally substituted with a lower alkyl group or a functional group.

The term aryl means an aryl group having from 6 to 20 carbon atoms (such as but not limited to phenyl, tolyl, xylyl, cumenyl, naphthyl), optionally substituted with a lower alkyl group or a functional group, or a fused aryl or a heteroaryl group having from 6 to 20 carbon atoms (such as but not limited to furyl, thienyl, pyrrolyl, imidazolyl, pyridyl, pyrazyl, pyrimidinyl, indolyl, carbazolyl, isoxazolyl, isothiazolyl).

The term alkylaryl means an alkylaryl group having from 6 to 20 carbon atoms (such as but not limited to benzyl, phenethyl, naphthylmethyl) optionally substituted with a lower alkyl group or a functional group.

The term alkaloyl means preferably —COR1 wherein R1 is an alkyl group as defined above (such as but not limited to acetyl, propionyl or pivaloyl).

The term aryloyl means preferably —COR1 wherein R1 is an aryl group as defined above (such as but not limited to benzoyl or phenylacetyl).

The term lower alkyl means a straight or branched alkyl group having from 1 to 8 carbons atoms (such as but not limited to methyl, ethyl, n-propyl, isopropyl, n-butyl, iso-butyl, sec-butyl or tert-butyl).

The term functional group means an halogen, —OH, —OR3, —CN, —COOR3, —COR3, —CONR3R4, —OCOR3, —NH2, —NHR3, —NR3R4, —NHCOR3 and —N(COR3)2, —NO2, —SH, —SR3, wherein R3 and R4 are independently a lower alkyl, an alkylaryl or an aryl group as defined previously. The term halogen means an atom like chlorine, bromine, flourine or iodine.

The optically active catalyst used in the asymmetric hydrogenation of the en-amide derivative of formula (III) is represented by a chiral phosphine transition metal complexe of formula (VIIA) or formula (VIIB):

(VIIA)

or

(VIIB)

wherein

M is a transition metal selected in the group comprising ruthenium (Ru), rhodium (Rh) and iridium (Ir) preferably M is ruthenium or rhodium.

X is a halogen atom selected in the group comprising chlorine (Cl), bromine (Br), fluorine (F) and iodine (I), preferably X is chlorine or bromine.

Z is an aryl group having from 6 to 20 carbon atoms or an unsaturated organic group, cyclic or not, selected in the group comprising olefine, diene and cyano, preferably diene and most preferably cyclooctadiene (COD).

L* is a chiral ligand selected in the group comprising the chiral diphosphine derivatives, the chiral atropoisomeric diphosphine derivatives, the chiral monodentate phosphoramidine derivatives, the chiral biphospholane derivatives, the chiral ferrotane derivatives and the chiral ferrocenyl phosphine derivatives, Y is an anion such as $ClO_4^-$, $BF_4^-$, $PF_6^-$, $SbF_6^-$, preferably $BF_4^-$.

S is a dialkyl ammonium, preferably a dimethyl ammonium.

j is an integer equal to 0 or 1.

is an integer equal to 0, 1, 2 or 4.

n is an integer equal to 1 or 2.

The transition metal preferably means ruthenium or rhodium.

The aryl group is a benzene optionally substituted with an alkyl.

The olefin is selected in the group comprising pi-allyl and 1,3,5,7-cyclooctatetraene and the diene is selected in the group comprising 1,3-butadiene, 2,5-norbornadiene, 1,5-cyclooctadiene (COD) and cyclopentadiene.

The chiral diphosphine is selected in the group comprising BICP, DuPHOS, MiniPHOS, BDPMI, TangPHOS, P-PHOS, Tol-P-PHOS, Xyl-P-PHOS and BPE.

The chiral atropoisomeric diphosphine is selected in the group comprising BINAP, TolBINAP, MeOBIPHEP, BINAPO, SYNPHOS and BINAPO optionally ortho-substituted with an alkyl or an aryl.

The chiral monodentate phosphoramidine is selected in the group comprising Monophos and Ethylmonophos.

The chiral bisphospholane is selected in the group comprising Tangphos, Duphos, Me-Duphos, Me-BPE, Et-BPE, Binaphane and Malphos.

The chiral ferrocenyl phosphine is JOSIPHOS.

The chiral ligand is preferably a chiral atropoisomeric diphosphine or a chiral bisphospholane, most preferably BINAP, MeOBIPHEP, Tangphos, Me-BPE, Et-BPE or Binaphane.

The wellknown abbreviations listed above have the following meaning:

Concerning the Chiral Diphosphine Derivatives:
BICP: (R,R)-2,2'-bis-diphenylphosphanyl-bicyclopentyl and other isomers.
MiniPHOS: 1,3-diphenyl-[1,3]diphospholane and other isomers.
BDPMI: 2-Imidazolidinone, 4,5-bis[(diphenylphosphino)methyl]-1,3-dimethyl-, (4S,5S)- and other isomers.
TangPHOS: 2,2'-Biphospholane, 1,1'-bis(1,1-dimethylethyl)-, (1S,1'S,2R,2'R) and other isomers.
P-PHOS: 3,3'-Bipyridine, 4,4'-bis(diphenylphosphino)-2,2',6,6'-tetramethoxy-, (3S); or 3,3'-Bipyridine, 4,4'-bis(diphenylphosphino)-2,2',6,6'-tetramethoxy-, (3R);
Tol-P-PHOS: 3,3'-Bipyridine, 4,4'-bis(di-(4-methylphenyl)-phosphino)-2,2',6,6'-tetramethoxy-, (3S); or 3,3'-Bipyridine, 4,4'-bis(di-(4-methylphenyl)-phosphino)-2,2',6,6'-tetramethoxy-, (3R);
Xyl-P-Phos: 3,3'-Bipyridine, 4,4'-bis(di-(3,5-dimethylphenyl)-phosphino)-2,2',6,6'-tetramethoxy-, (3S); or 3,3'-Bipyridine, 4,4'-bis(di-(3,5-dimethylphenyl)-phosphino)-2,2',6,6'-tetramethoxy-, (3R).
BPE: 1,2-bis(substituted-phospholano)ethane and other isomers.
Me-BPE: 1,2-(2,5-dimethylphospholano)ethane and other isomers Concerning the Atropoisomeric Chiral Diphosphines Derivative:
BINAP: (R)-2,2'-Bis(diphenylphosphino)-1,1'-binaphthyl or (S)-2,2'-Bis(diphenylphospbino)-1,1'-binaphthyl;
TolBINAP: (R)-2,2'-Bis(di-p-tolylphosphino)-1,1'-binaphthyl or (S)-2,2'-Bis(di-p-tolylphosphino)-1,1'-binaphthyl;
MeOBIPHEP: (R)-2,2'-bis-diphenylphosphanyl-6,6'-dimethoxy-biphenyl or (S)-2,2'-bis-diphenylphosphanyl-6,6'-dimethoxy-biphenyl;
BINAPO: (R)-[1,1'-Binaphthalene]-2,2'-diyl bis(diphenylphosphinite) or (S)-[1,1'-Binaphthalene]-2,2'-diyl bis(diphenylphosphinite);
SYNPHOS: -(R)-[2,3,2',3'-tetrahydro-5,5'-bi(1,4-benzodioxin)-6,6'-diyl]bis(diphenylphosphane) or -(S)-[2,3,2',3'-tetrahydro-5,5'-bi(1,4-benzodioxin)-6,6'-diyl]bis(diphenylphosphane)

Concerning the Chiral Monodentate Phosphoramidine Derivative:
Monophos: Dinaphtho [2,1-d:1',2'-f][1,3,2]dioxaphosphepin-4-amine, N,N-dimethyl-,(2aR); or Dinaphtho [2,1-d:1',2'-f][1,3,2]dioxaphosphepin-4-amine, N,N-dimethyl-,(11bS);

Concerning the Chiral Bisphospholane Derivative:
Me-Duphos: 1,2-bis-((2R,5R)-2,5-dimethylphospholano)benzene or 1,2-bis-((2S,5S)-2,5-dimethylphospholano)benzene;
DupHOS: bis(substituted-phospholano)benzene;

Concerning the Chiral Ferrocenyl Phosphine Derivative:
JOSIPHOS: (R)-1-[(S)-2-diphenylphosphino)-ferrocenyl]ethyldicyclohexylphosphine or (S)-1-[(R)-2-diphenylphosphino)-ferrocenyl]ethyldicyclohexylphosphine.

According to a preferred embodiment of the invention, the optically active catalyst of formula (VII) is $Ru(COD)(MeOBIPHEP)BF_4^-$, $Ru(COD)(BINAP)BF_4^-$ or $Rh(COD)(Me-BPE)BF_4^-$. The catalyst can be in situ prepared or can a preformed complex.

The solvent used during the asymmetric hydrogenation is selected in the group comprising ether such as tetrahydrofuran (THF), tetrahydropyran and diethyl ether, aromatic hydrocarbon such as benzene and toluene, halogenated hydrocarbon such as dichloromethane, alcohol such as methanol, ethanol or isopropanol. According to a preferred embodiment of the invention the solvent used is an alcohol, more preferably methanol.

The molar ratio of the en-amide derivative of formula (III) to the optically active catalyst (VII) used during the asymmetric hydrogenation is from 100/1 to 10000/1, preferably from 100/1 to 1000/1, more preferably from 200/1 to 1000/1, especially from 500/1 to 1000/1.

The hydrogen pressure used during the asymmetric hydrogenation is from 0.5 to 20 bar, preferably from 0.5 to 10 bar, more preferably 1 to 8 bar, especially from 4 to 8 bar.

The temperature range used during the asymmetric hydrogenation is from −20 to 100° C., preferably from 20 to 100° C., more preferably from 20° C. to 60° C. and especially from 40° C. to 60° C., for a period of time in the range of 10 min to three days, preferably of one hour to three days, more preferably 1 hours to 1 day and especially 4 hours to 1 day.

The step of the hydrolysis reaction of the amide derivative of formula (II) obtained at the end of the assymetric hydrogenation is performed in presence of an organic acid or a mineral acid such as hydrochloric acid, sulfuric acid or hydrobromic acid, preferably sulfuric acid, according to methods described in the literature to obtain alpha-aminoindan derivatives of formula (I) in an appropriate solvent, preferably an alcohol and more preferably methanol.

According to a preferred embodiment of the invention, the en-amide derivative of formula (III) is prepared by the two following step:

an acylation reaction of an alpha-hydroxyimino-indane derivative of formula (V):

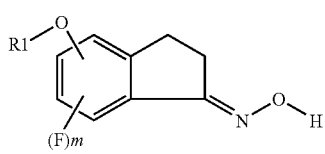

(V)

wherein $R_1$ and m are as defined above
in presence of an organic anhydride of formula (VI):

$R_2OC—O—COR'_2$ (VI)

wherein $R_2$ and $R'_2$ identical or different are a hydrogen atom, an alkyl group having from 1 to 20 carbon atoms, an aryl group having from 6 to 20 carbon atoms, an alkylaryl group having from 6 to 20 carbon atoms, preferably R2 and R'2 are an alkyl group having from 1 to 20 carbon atoms, and more preferably a methyl.

in order to obtain an N-(O-acylimino)-indane derivative of formula (IV):

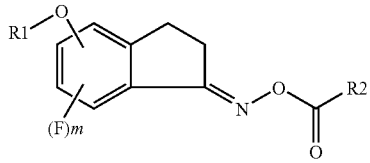

(IV)

wherein $R_1$, m and $R_2$ are as defined above,
a hydrogenolyse-acylation reaction of the N-(O-acylimino)-indane derivative of formula (IV) obtained in the previous step,
in presence of an organic anhydride of formula (VI) as defined above and of an heterogeneous catalyst based on a metal transition selected in the group comprising Pt, Pd, Ir, Rh and Ni,
in order to obtain an en-amide derivative of formula (III).

The molar ratio of the organic anhydride of formula (VI) to the alpha-hydroxyimino-indane derivative of formula (V) used during the acylation reaction is from 1:1 to 5:1, and is more preferably 1.5:1 to 2:1.

The acylation reaction is performed under a temperature range from 0 to 80° C., preferably 20° C. to 40° C., for a period of time in the range of 1 to 8 hours, preferably 2 to 4 hours.

The heterogeneous catalyst used during the hydrogenolysis-acylation reaction of the derivative of formula (IV) is selected in the group comprising $PtO_2$, Pt/C, Pd/C, $Pd(OH)_2$/C, Ir/C, Rh/C and Raney Ni.

Preferably the heterogeneous catalyst is Ir/C.

The effective amount of the heterogeneous catalyst used during the hydrogenolysis-acylation is in an amount from 0.1% to 30% for 1 mole of the N-(O-acylimino)-indane derivative of formula (IV).

The reaction of hydrogenolysis-acylation is performed with a hydrogen pressure range from 0.5 to 20 bars under a temperature range from −20 to 150° C., preferably 20 to 120° C., for a period of time in the range from 10 min to three days, preferably from 1 to 24 hours.

The molar ratio of the organic anhydride of formula (VI) to the N-(O-acylimino)-indane derivative of formula (IV) used during the hydrogenolyse-acylation reaction is from 1:1 to 5:1 and preferably 1.5:1 to 2:1.

The acylation reaction of the derivative of formula (V) and the hydrogenolysis-acylation reaction of the derivative of formula (IV) are respectively performed in an aprotic non-basic solvent selected in the group comprising ether like tetrahydrofuran (THF) and diethyl ether, organic acid alkyl ester like ethyl acetate, aromatic hydrocarbon like toluene, and halogenated hydrocarbon like methylene chloride. Preferably the aprotic non-basic solvent is an ether, more preferably THF.

The organic anhydride of formula (VI) used during the acylation reaction and the hydrogenolysis-acylation reaction is selected in the group comprising dialkyl anhydride, diaryl anhydride and alkylarylanhydride, and is preferably an acetic anhydride. The preferred organic anhydride is acetic anhydride.

The derivatives of formula (V) (alpha-hydroxyimino-indane) or (IV) (N-(O-acylimino)-indane)) may be used as a syn-form, anti-form or a mixed form of both.

In a preferred embodiment, the two step previously described (the acylation reaction of the derivatives of formula (V) and the hydrogenolysis-acylation reaction of derivatives of formula (IV)) are carried out in one step (also called "one pot" process).

Thus, the derivative of formula (III) is obtained directly from the derivative of formula (V) without isolating specifically the derivative of formula (IV).

The present invention has also for object the en-amide derivative of formula (III):

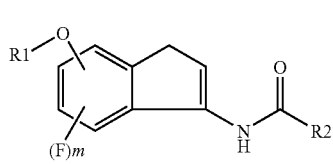

(III)

wherein
m is an integer equal to 0, 1, 2 or 3, $R_1$ is a hydrogen atom, an alkyl group having from 1 to 20 carbon atoms, an aryl group having from 6 to 20 carbon atoms, an alkylaryl group having from 6 to 20 carbon atoms, an alkaloyl group, an aryloyl group, preferably R1 is an alkyl group having from 1 to 20 carbon atoms, more preferably R1 is an alkyl group having from 1 to 4 carbon atoms, $R_2$ is an hydrogen, an alkyl group having from 1 to 20 carbon atoms, an aryl group having from 6 to 20 carbon atoms, an alkylaryl group having from 6 to 20 carbon atoms, preferably $R_2$ is an alkyl group having from 1 to 20 carbon atoms.

The present invention has also for object the optically active substituted alpha-amino indane derivatives of formula (I):

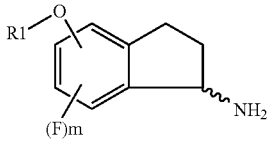

wherein
m is an integer equal to 0, 1, 2 or 3,
$R_1$ is a hydrogen atom, an alkyl group having from 1 to 20 carbon atoms, an aryl group having from 6 to 20 carbon atoms, an alkylaryl group having from 6 to 20 carbon atoms, an alkaloyl group, an aryloyl group, preferably R1 is an alkyl group having from 1 to 20 carbon atoms, and more preferably R1 is an alkyl group having from 1 to 4 carbon atoms, as synthetic intermediates for the preparation of active pharmaceuticals.

DETAILED DESCRIPTION

Brief Description of the Drawings

The FIG. 1 is an illustration of the different steps of the new process of the invention for the synthesis of substituted alpha-aminoindan derivatives. The first step of the process relates to acetylation of the corresponding oxime function of the derivatives of formula (V) in the presence of an organic anhydride of formula (VI) in an appropriate solvent to obtain the derivatives of formula (IV).

The second step of the process relates to a hydrogenolysis-acylation of the intermediates of formula (IV) in presence of a heterogeneous catalyst based on a metal transition and an organic anhydride of formula (VI) in an appropriate solvent to obtain the derivatives of formula (III).

Figure 1:
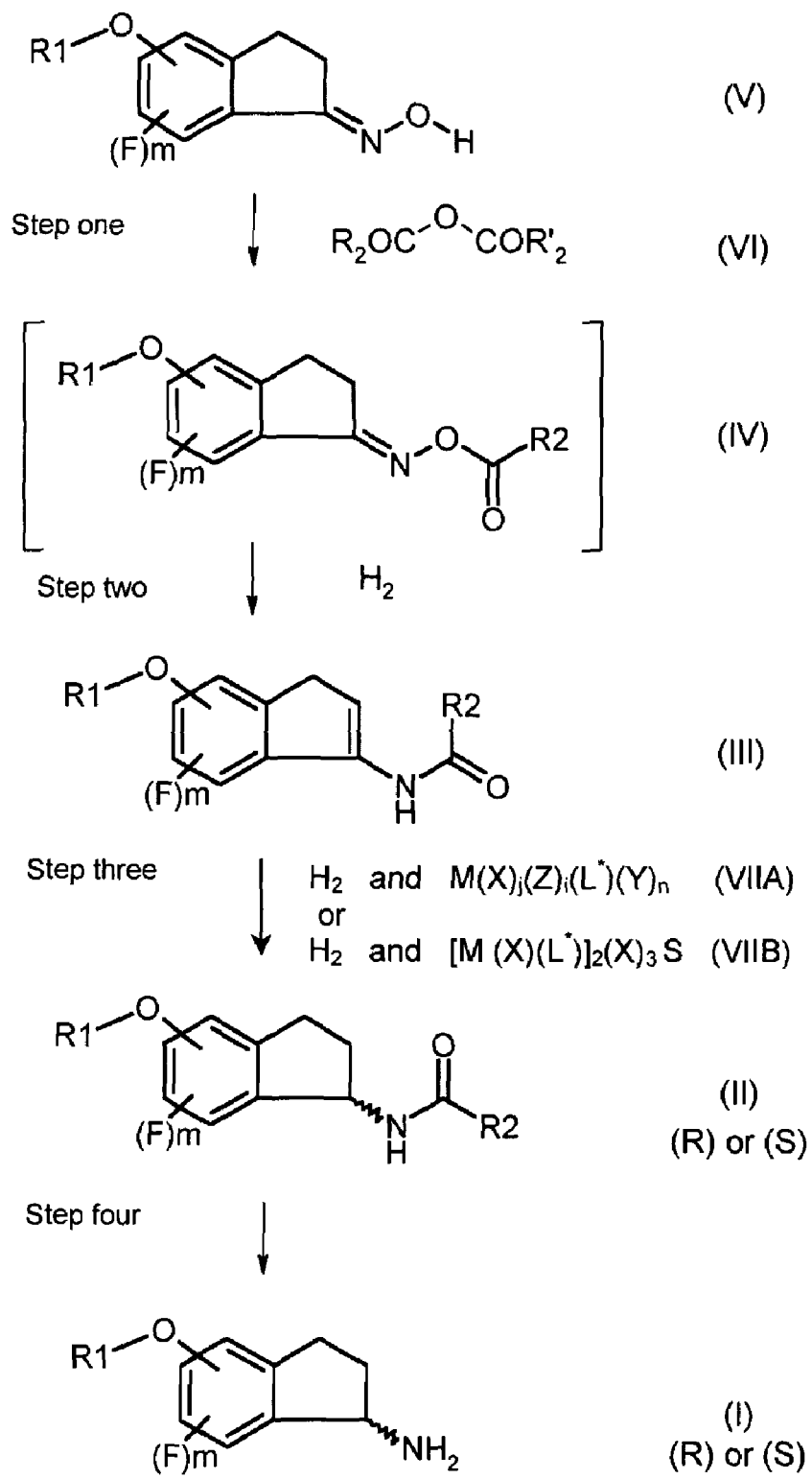

The third step of the process relates to an asymmetric hydrogenation reaction of the derivatives of formula (III) in presence of hydrogen and optically active catalyst of formula (VII) and an appropriate solvent to obtain optically active alpha-indanyl amide derivatives of formula (II).

The fourth step is a hydrolysis reaction of derivatives of formula (II) to obtain alpha-amino-indan derivatives of formula (I).

The invention will be better understood from the experimental details described in the following examples, which will not limit the scope of the invention in any way.

EXAMPLE 1

Acetylation Reaction

Preparation of Indan-1-on-(O-acetyloxime), methoxy-6 of Formula (IV) (in which R1=R2=Ch$_3$, m=0)

6-methoxy-indan-1-one-oxime of formula (V) (in which $R_1$=CH$_3$, m=0) (30 g, 0.169 mol) is partially dissolved in 180 ml of THF at room temperature. To this solution, acetic anhydride of formula (VI) in which $R_2$=R'$_2$=CH$_3$ (47.9 ml, 0.508 mol) is added in 15 minutes at 20° C. The reaction mixture is stirred between 20-30° C. during 2 hours and is then concentrated. A colorless liquid is obtained which can solidify. The residue is dissolved in methylene chloride (60 ml). The organic layer is washed with water (60 ml) twice. The organic layer is respectively separated from the aqueous layer, is dried over MgSO4, is filtered off and is concentrated to obtain 56 g of a white solid product (the indan-1-on-(O-acetyloxime), methoxy-6 of formula (IV)). This product is partially dissolved in MTBE (tert-butyl-methyl ether) (60 ml), is warmed at 55° C. MTBE (195 ml) is added again slowly to dissolve completely the product. The solution is warmed at reflux temperature during 5 nm. The solution is cooled at room temperature (20° C.) and the solid is filtered off. The solid is dried under vacuum.

28.8 g of white solid (the indan-1-on-(O-acetyloxime), methoxy-6 of formula (IV)) is obtained. The yield is 77%.

EXAMPLE 2

The Preparation of the Acetamide, N-(2,3-dihydro-6-methoxy-1H-inden-1-yl) of Formula (III) in which R1=R2=CH3, m=0

This example illustrates a "one pot" process from oxime derivative of formula (V) (in which $R_1$=CH$_3$, m=0).

25 g (0.141 mol) of 6-methoxy-indan-1-one-oxime of formula (V) (in which $R_1$=CH$_3$, m=0) was dissolved in 190 ml of THF.

The mixture is stirred at room temperature until complete dissolution of the product. Then 40 ml of acetic anhydride of formula (VI) in which $R_2$=R'$_2$=CH$_3$ are added drop wise. The reaction mixture is stirred at a temperature between 20-30° C. during 2 hours. 2.5 g of the Ir-carbon (5%) catalyst is added to this reaction mixture. The hydrogenation is carried out at a hydrogen pressure of 7.4 bars at 70-80° C. during 2 hours 15 minutes. After the catalyst Ir/C is filtered off, the filtrate was concentrated to dryness under reduced pressure. The residue is dissolved in 400 ml of toluene and concentrated to dryness under reduced pressure. The residue is dissolved in 75 ml of toluene, the mixture is stirred at a temperature 20° C. during 15 nm. The mixture is filtered. The solid is dried under reduced pressure at a temperature of 40-45° C.

The compound Acetamide, N-(2,3-dihydro-6-methoxy-1H-inden-1-yl)- is obtained with 84% yield. The chemical purity is 98.4%.

EXAMPLE 3

Preparation of N-(6-methoxy-indan-1-yl)-acetamide (R) of Formula (II) (in which $R_1$=R2=CH$_3$ and m=0)

The molar ratio of the en-amide derivative of formula (III) to the catalyst (VII) during the asymmetric hydrogenation is 500/1.

3 g (0.0148 mol) of N-(6-methoxy-3H-inden-1-yl)-acetamide of formula (III) (in which $R_1$=CH$_3$ and m=0) was dissolved in 30 ml of methanol and 24 mg (2.95 10$^{-5}$ mol) of (R)-Ru(OAc)$_2$(MeOBIPHEP) of formula (VII) are added. The reaction mixture is flushed with nitrogen (5 times) and is warmed to 40° C. The hydrogenation is carried out with a hydrogen pressure of 8 bars at a temperature of 40° C. during 27 hours.

The reaction mixture is concentrated until complete removal of the methanol. 50 ml of toluene are added to the residue and concentrated to dryness. The operation is repeated with 10 ml and 5 ml of toluene. The solid is dried under vacuum.

The yield is 89% and the enantiomeric excess (e.e.) is 84.5%. Then the product is recrystallized in 15 ml of toluene. The yield is 80% and the enantiomeric excess (e.e.) is >98%.

EXAMPLE 4

Preparation of N-(6-methoxy-indan-1-yl)-acetamide (R) of Formula (II) (in which $R_1=CH_3$ and m=0)

The reaction is carried out in the same manner as in example 3, except that the molar ratio of the en-amide derivative of formula (III) to the catalyst (VII) during the asymmetric hydrogenation is 100/1 and the hydrogenation is carried out at 30° C.

The yield is 95% and the enantiomeric excess (e.e.) is 86.6%. Then the product is recrystallized in toluene. The yield is 77% and the enantiomeric excess is 98.2%.

EXAMPLE 5

Preparation of 6-methoxy-indan-1-ylamine (R) of Formula (I) (in which $R_1=CH_3$ and m=0)

1.5 g of N-(6-methoxy-indan-1-yl)-acetamide (R) of formula (II) (in which $R_1=CH_3$ and m=0) is dissolved in methanol (13 ml). To this methanolic solution of the product a solution of hydrochloric acid 36% is added (2.2 ml). The mixture is warmed at 90° C. during 8 hours.

After the mixture is cooled down to 25° C., a solution of hydrochloric acid (1.1 ml) is added again and the mixture is warmed at 90° C. during 7 hours. After the mixture is cooled down to 25° C., the same operation is repeated with the solution of hydrochloric acid (0.5 ml) and the mixture is warmed at 90° C. during 6 hours. The mixture is concentrated to remove the methanol. Water is added (6.5 ml) to the residue and the mixture is concentrated until the complete removal of methanol. The mixture is warmed at 60° C. and water (7 ml) is added to complete dissolution of the product. Toluene (8 ml) is added to the solution. After removal of the organic layers, the aqueous layer is basified with soda 30% until a pH range 12 to 13 in presence of xylenes (5 ml) at a temperature 22° C. The aqueous layer is separated and re-extracted with xylenes (8 ml) 3 times. All organic layers are mixed and concentrated to dryness. The product is obtained with 65% yield.

Asymmetric hydrogenation reactions were performed using different ligand and conditions according to the protocol of Example 3. The results are summarized in the following table for each example.

| Ex. | chiral ligand | S/C | Pressure $H_2$ bar | Temp. °C. | Time | % e.e. |
|---|---|---|---|---|---|---|
| 6 | (1S,1S', 2R,R') Tangphos 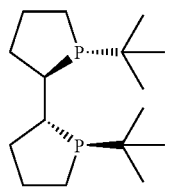 | 110 | 6 | 25 | 45 mn | 93.8% (R) |
| 7 | (1S,1S', 2R,R') Tangphos 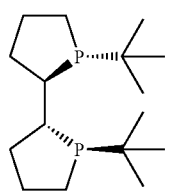 | 1000 | 12 | 25 | 18 h | 89.8% (R) |

-continued
| Ex. | chiral ligand | S/C | Pressure H₂ bar | Temp. °C. | Time | % e.e. |
|---|---|---|---|---|---|---|
| 8 | (S) Binaphane 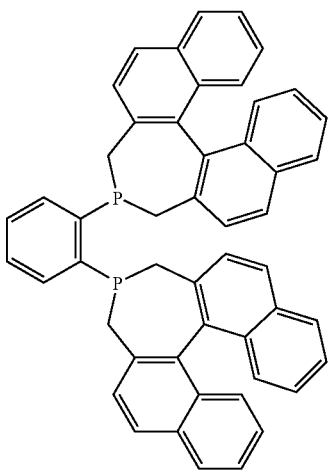 | 110 | 6 | 25 | 45 mn | 95.8% (R) |
| 9 | (R,R) 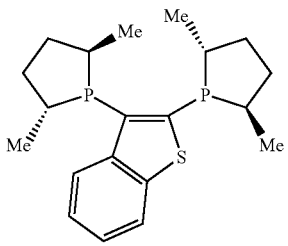 | 110 | 6 | 25 | 10-12 h | 72.3% (R) |
| 10 preformed catalyst | (S,S) 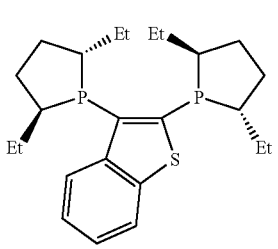 | 110 | 6 | 25 | 1-1 h 30 | 84.2% (S) |
| 11 preformed catalyst | (R,R) MeBPE 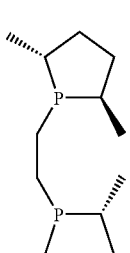 | 110 | 6 | 25 | 15 mn | 97.9% (R) |

| Ex. | chiral ligand | S/C | Pressure H$_2$ bar | Temp. °C. | Time | % e.e. |
|---|---|---|---|---|---|---|
| 12 | (R,R) MeBPE | 110 | 6 | 25 | 30 mn | 98.2% (R) |
| 13 preformed catalyt | (R,R) MeBPE | 10000 | 6 | 50 | 24 h | 95.2% (R) |
| 14 | (R,R) EtBPE | 110 | 6 | 25 | 45 mn | 97% (R) |

The invention claimed is:

1. A process for the preparation of an optically active substituted alpha-amino indane compound of formula (I):

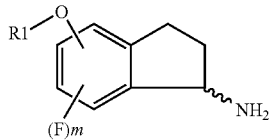

(I)

wherein m is an integer selected from 0, 1, 2 and 3,

R$_1$ is selected from the group consisting of a hydrogen atom; an alkyl group having from 1 to 20 carbon atoms; an aryl group having from 6 to 20 carbon atoms; an alkylaryl group having from 6 to 20 carbon atoms; an alkaloyl group; and an aryloyl group, said method comprising:

a) an asymmetric hydrogenation reaction of an en-amide compound of formula (III)

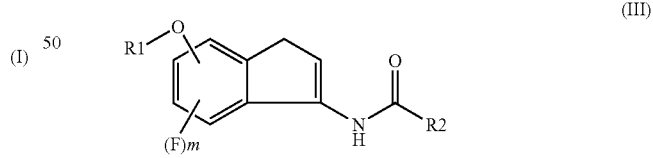

(III)

wherein m and R1 are as defined above,

R2 is selected from the group consisting of a hydrogen atom; an alkyl group having from 1 to 20 carbon atoms; an aryl group having from 6 to 20 carbon atoms; and an alkylaryl group having from 6 to 20 carbon atoms, in presence of hydrogen and of an optically active catalyst, represented by a chiral phosphine transition metal complex of formula (VIIA) or (VIIB):

(VIIA)

(VIIB)

wherein
- M is a transition metal selected from the group consisting of ruthenium (Ru), rhodium (Rh) and iridium (Ir)
- X is a halogen atom selected from the group consisting of chlorine (Cl), bromine (Br), fluorine (F) and iodine (I),
- Z is selected from an aryl group having from 6 to 20 carbon atoms; an unsaturated organic group, and an unsaturated cyclic organic group, said unsaturated organic group being selected from the group consisting of an olefin, a diene and Cyano,
- Y is an anion selected from the group consisting of $ClO_4^-$, $BF_4^-$, $PF_6^-$, and $SbF_6^-$,
- j is an integer selected from 0 and 1,
- i is an integer selected from the group consisting of 0, 1, 2 and 4,
- n is an integer selected from 1 and 2,
- S is a primary amine,
- L* is a chiral diphosphine ligand selected from the group consisting of BICP, DuPHOS, MiniPHOS, BDPMI, TangPHOS, P-PHOS, Tol-P-PHOS, Xyl-P-PHOS and BPE; a chiral atropoisomeric diphosphine ligand selected from the group consisting of BINAP, TolBINAP, MeOBIPHEP, BINAPO, SYNPHOS and BINAPO optionally ortho-substituted with a substituent selected from an alkyl and an aryl; a chiral monodentate phosphoramidine; a chiral biphospholane; a chiral ferrotane or a chiral ferrocenyl phosphine, to obtain an amide compound of formula (II):

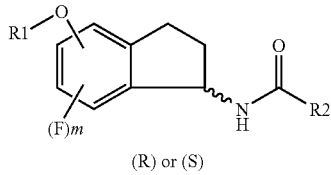

(II)

(R) or (S)

b) a hydrolysis reaction of the amide compound of formula (II) obtained in step a), thereby obtaining said optically active substituted alpha-amino indane compound of formula (I).

2. The process of claim 1, wherein the olefin is selected from the group consisting of pi-allyl and 1,3,5,7-cyclooctatetraene; and the diene is selected from the group consisting of 1,3-butadiene, 2,5-norbornadiene, 1,5-cyclooctadiene (COD) and cyclopentadiene.

3. The process of claim 1, wherein the chiral monodentate phosphoramidine is selected from the group consisting of Monophos and Ethylmonophos.

4. The process of claim 1, wherein the chiral bisphospholane is selected from the group consisting of Tangphos, Duphos, Me-Duphos Me-BPE, Et-BPE, Binaphane and Malphos.

5. The process of claim 1, wherein the chiral ferrocenyl phosphine is JOSIPHOS.

6. The process of claim 1, wherein the solvent used during the asymmetric hydrogenation is selected from the group consisting of an ether, and aromatic hydrocarbon and halogenated hydrocarbon and an alcohol.

7. The process of claim 6, wherein the ether is selected from the group consisting of tetrahydrofuran (THF), tetrahydropyran and diethyl ether; the aromatic hydrocarbon is selected from the group consisting of benzene and toluene; the halogenated hydrocarbon is dichloromethane, the alcohol is selected from the group consisting of methanol, ethanol and isopropanol.

8. The process of claim 1, wherein the molar ratio of the en-amide compound of formula (III) to the optically active catalyst used during the asymmetric hydrogenation is ranging between 100/1 and 10000/1.

9. The process of claim 1, wherein the molar ratio of the en-amide compound of formula (III) to the optically active catalyst ranges between 100/1 and 1000/1.

10. The process of claim 1, wherein the molar ratio of the en-amide compound of formula (III) to the optically active catalyst ranges between 200/1 and 1000/1.

11. The process of claim 1, wherein the hydrogen pressure ranges between 0.5 and 20 bars.

12. The process of claim 1, wherein the hydrogen pressure ranges between 0.5 and 10 bars.

13. The process of claim 1, wherein the hydrogen pressure ranges between 1 and 8 bars.

14. The process of claim 1, wherein in step a) the temperature ranges between −20 and 100° C.

15. The process of claim 1, wherein in step a) the temperature ranges between 20 and 100° C.

16. The process of claim 1, wherein in step a) the temperature ranges between 20° C. and 60° C.

17. A process for the preparation of an optically active substituted alpha-amino indane compound of formula (I):

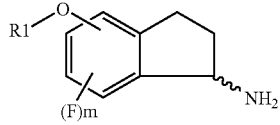

(I)

wherein
- m is an integer selected from 0, 1, 2 and 3,
- $R_1$ is selected from the group consisting of a hydrogen atom; an alkyl group having from 1 to 20 carbon atoms; an aryl group having from 6 to 20 carbon atoms; an alkylaryl group having from 6 to 20 carbon atoms; an alkaloyl group; and an aryloyl group, said method comprising:
a) an asymmetric hydrogenation reaction of an en-amide compound of formula (III)

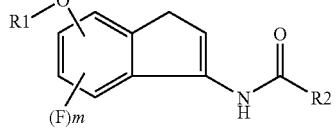

(III)

wherein m and R1 are as defined above,
R2 is selected from the group consisting of a hydrogen atom; an alkyl group having from 1 to 20 carbon atoms; an aryl group having from 6 to 20 carbon atoms; and an alkylaryl group having from 6 to 20 carbon atoms, in presence of hydrogen and of an optically active catalyst selected from group consisting of Ru(COD)(MeOBIPHEP)BF$_4^-$, Ru(COD)(BINAP)BF$_4^-$ and Rh(COD)(Me-BPE)BF4$^-$, to obtain an amide compound of formula (II):

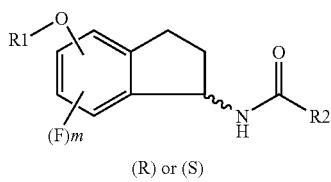

b) a hydrolysis reaction of the amide compound of formula (II) obtained in step a), thereby obtaining said optically active substituted alpha-amino indane compound of formula (I).

18. A process for the preparation of an optically active substituted alpha-amino indane compound of formula (I):

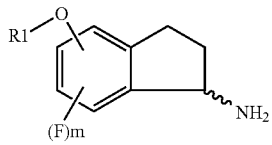

wherein m is an integer selected from 0, 1, 2 and 3,

R$_1$ is selected from the group consisting of a hydrogen atom; an alkyl group having from 1 to 20 carbon atoms; an aryl group having from 6 to 20 carbon atoms; an alkylaryl group having from 6 to 20 carbon atoms; an alkaloyl group; and an aryloyl group, said method comprising the following steps:

an acylation reaction of an alpha-hydroxyimino-indane derivative of formula (V):

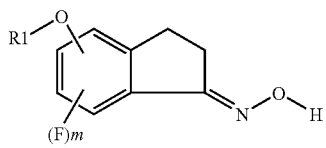

wherein R$_1$ and m are as defined above in presence of an organic anhydride of formula (VI):

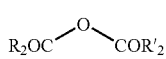

wherein R2 and R'2 identical or different are selected from the group consisting of a hydrogen atom, an alkyl group having from 1 to 20 carbon atoms, an aryl group having from 6 to 20 carbon atoms, and an alkylaryl group having from 6 to 20 carbon atoms, in order to obtain an ester oxime compound of formula (IV):

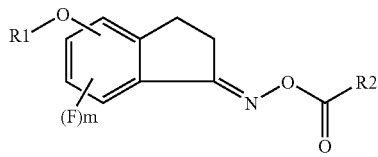

wherein R$_1$, m and R$_2$ are as defined above, a hydrogenolysis-acylation reaction of the ester oxime compound of formula (IV) obtained in the previous step, in presence of an organic anhydride of formula (VI) as defined above and of an heterogeneous catalyst comprising a transition metal selected from the group consisting of Pt, Pd, Ir, Rh and Ni, to obtain an en-amide compound of formula (III):

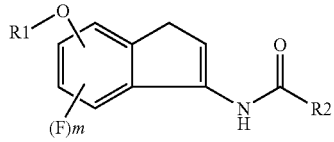

wherein m, R1 and R2 are as defined above, an asymmetric hydrogenation reaction of the en-amide compound of formula (III) obtained in the previous step, in presence of hydrogen and of an optically active catalyst, to obtain an amide compound of formula (II):

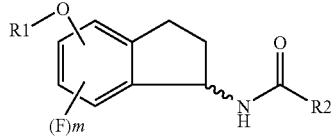

a hydrolysis reaction of the amide compound of formula (II) obtained in the previous step, thereby obtaining said optically active substituted alpha-amino indane compound of formula (I).

19. The process of claim 18, wherein the molar ratio of the organic anhydride of formula (VI) to the alpha-hydroxyimino-indane of formula (V) used during the acylation reaction is ranging from 1:1 to 5:1.

20. The process of claim 18, wherein the heterogeneous catalyst used during the hydrogenolysis-acylation reaction of the derivative of formula (IV) is selected from the group consisting of PtO$_2$, Pt/C, Pd/C, Pd(OH)$_2$/C, Ir/C, Rh/C and Raney Ni.

21. The process of claim 18, wherein the effective amount of the heterogeneous catalyst used during the hydrogenolysis-acylation is ranging between 0.1% and 30% for 1 mole of the ester oxime compound of formula (IV).

22. The process of claim 18, wherein the molar ratio of the organic anhydride of formula (VI) to the ester oxime compound of formula (IV) used during the hydrogenolysis-acylation reaction ranges between 1:1 and 5:1.

23. The process of claim 18, wherein the acylation reaction of the compound of formula (V) and the hydrogenolysis-acylation reaction of the compound of formula (IV) are respectively performed in an aprotic non-basic solvent selected from the group consisting of an ether, and organic acid alkyl ester, an aromatic hydrocarbon and a halogenated hydrocarbon.

24. The process of claim 18, wherein the organic anhydride of formula (VI) used during the acylation reaction and the hydrogenolysis-acylation reaction is selected from the group consisting of a dialkyl anhydride, a diaryl anhydride and an alkylarylanhydride.

25. The process of claim 18, wherein the organic anhydride is acetic anhydride.

26. The process of claim 18, wherein the derivative of formula (III) is obtained directly from the derivative of formula (V) without isolating specifically the derivative of formula (IV).

27. The process of claim 18 wherein the optically active catalyst comprises a chiral phosphine transition metal complex of formula (VIIA):

wherein

M is a transition metal selected from the group consisting of ruthenium (Ru), rhodium (Rh) and iridium (Ir)

X is a halogen atom selected from the group consisting of chlorine (Cl), bromine (Br), fluorine (F) and iodine (I), Z is selected from an aryl group having from 6 to 20 carbon atoms; an unsaturated organic group, and an unsaturated cyclic organic group, said unsaturated organic group being selected from the group consisting of an olefin, a diene and Cyano;

L* is a chiral ligand selected from the group consisting of a chiral diphosphine; a chiral atropoisomeric diphosphine, a chiral monodentate phosphoramidine, a chiral biphospholane, a chiral ferrotane and a chiral ferrocenyl phosphine, Y is an anion selected from the group consisting of $ClO_4^-$, $BF_4^-$, $PF_6^-$, and $SbF_6^-$, j is an integer selected from 0 and 1, i is an integer selected from the group consisting of 0, 1, 2 and 4, n is an integer selected from 1 and 2.

28. The process of claim 27, wherein the chiral diphosphine is selected from the group consisting of BICP, DuPHOS, MiniPHOS, BDPMI, TangPHOS, P-PHOS, Tol-P-PHOS, Xyl-P-PHOS and BPE.

29. The process of claim 27, wherein the chiral atropoisomeric diphosphine is selected from the group consisting of BINAP, TolBINAP, MeOBIPHEP, BINAPO, SYNPHOS and BINAPO optionally ortho-substituted with a substituent selected from an alkyl and an aryl.

30. The process of claim 27, wherein the chiral monodentate phosphoramidine is selected from the group consisting of Monophos and Ethylmonophos.

31. The process of claim 27, wherein the chiral bisphospholane is selected from the group consisting of Tangphos, Duphos, Me-Duphos Me-BPE, Et-BPE, Binaphane and Malphos.

32. The process of claim 27, wherein the chiral ferrocenyl phosphine is JOSIPHOS.

33. The process of claim 18, wherein the optically active catalyst is selected from group consisting of Ru(COD)(MeO-BIPHEP)$BF_4^-$, Ru(COD)(BINAP)$BF_4^-$ and Rh(COD)(Me-BPE)$BF_4^-$.

* * * * *